United States Patent
Ghodousi et al.

(10) Patent No.: US 9,810,638 B2
(45) Date of Patent: Nov. 7, 2017

(54) SYSTEM AND METHOD FOR OPTICAL DETECTION USING CAPILLARY ACTION

(71) Applicant: RedXDefense, LLC, Rockville, MD (US)

(72) Inventors: Arman Ghodousi, Alexandria, VA (US); Sarah Josepha Toal, Gaithersburg, MD (US); Gregory Scott Ericksen, Silver Spring, MD (US); Daniel Douglas Montgomery, Washington, DC (US); Thomas Emory McVeigh, Shenandoah Junction, WV (US); Jacek Kotowicz, Washington, DC (US); Sean Conte, Gaithersburg, MD (US)

(73) Assignee: REDXDEFENSE, LLC, Rockville, MD (US)

( * ) Notice: Subject to any disclaimer, the term of this patent is extended or adjusted under 35 U.S.C. 154(b) by 81 days.

(21) Appl. No.: 14/298,639

(22) Filed: Jun. 6, 2014

(65) Prior Publication Data

US 2014/0287520 A1    Sep. 25, 2014

Related U.S. Application Data

(63) Continuation-in-part of application No. PCT/US2013/035121, filed on Apr. 3, 2013.
(Continued)

(51) Int. Cl.
*G01N 21/00* (2006.01)
*G01N 21/78* (2006.01)
(Continued)

(52) U.S. Cl.
CPC .......... *G01N 21/78* (2013.01); *G01N 15/0612* (2013.01); *G01N 21/8483* (2013.01);
(Continued)

(58) Field of Classification Search
None
See application file for complete search history.

(56) References Cited

U.S. PATENT DOCUMENTS

| 6,656,428 B1 | 12/2003 | Clark et al. |
| 7,629,885 B2 | 12/2009 | Dugan et al. |

(Continued)

OTHER PUBLICATIONS

Halim, M.I.A. et al. Analysis of Gunshot Residue Deposited on Cptton Cloth Target at Close Range Shooting Distances, 2010, Malaysian Journal of Forensic Science, vol. 1(1), pp. 48-53.*

(Continued)

*Primary Examiner* — Robert Xu
(74) *Attorney, Agent, or Firm* — Diederiks & Whitelaw, PLC

(57) ABSTRACT

A system and method for the detection of one or more analytes in a collected sample employs capillary action in a sample card containing a sample substrate, at least one test capsule and an absorbent pad. The absorbent pad absorbs the contents of the test capsule and delivers the same to the sample substrate, with the contents of the test capsule chemically reacting with at least one detection reagent to establish an optical indicator for the analyte(s). The sample card can be automatically tested within a reader device, which records and processes an optical signal produced by the chemical reaction and outputs a test result. The collected sample can then be further analyzed using a second device. Additionally, an adhesive component can be provided so that a sample can be collected thereon. Furthermore, the at least one detection reagent can include a surfactant.

29 Claims, 9 Drawing Sheets

Related U.S. Application Data

(60) Provisional application No. 61/619,674, filed on Apr. 3, 2012, provisional application No. 61/718,345, filed on Oct. 25, 2012.

(51) Int. Cl.
| | | |
|---|---|---|
| *G01N 21/84* | (2006.01) | |
| *G01N 33/22* | (2006.01) | |
| *G01N 15/06* | (2006.01) | |
| *G01N 15/00* | (2006.01) | |

(52) U.S. Cl.
CPC ..... *G01N 33/22* (2013.01); *G01N 2015/0096* (2013.01); *G01N 2015/0693* (2013.01); *G01N 2201/062* (2013.01)

(56) References Cited

U.S. PATENT DOCUMENTS

| | | |
|---|---|---|
| 2008/0145272 A1 | 6/2008 | Feaster et al. |
| 2010/0184229 A1 | 7/2010 | Haas et al. |
| 2010/0190268 A1 | 7/2010 | Jina |
| 2011/0236879 A1 | 9/2011 | Egan et al. |
| 2012/0211088 A1 | 8/2012 | Nelson et al. |

OTHER PUBLICATIONS

Battelle et al., A Literature Review of Wipe Sampling Methods for Chemical Warfare Agents and Toxic Industrial Chemicals, 2007. EPA/600/R-11/079 Jan. 2007.*

* cited by examiner

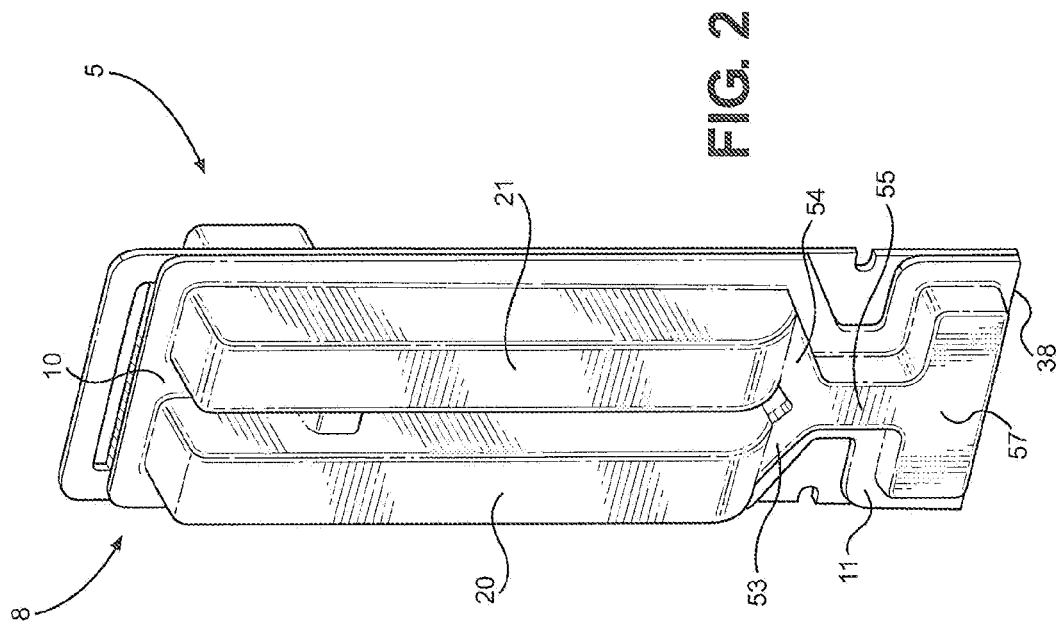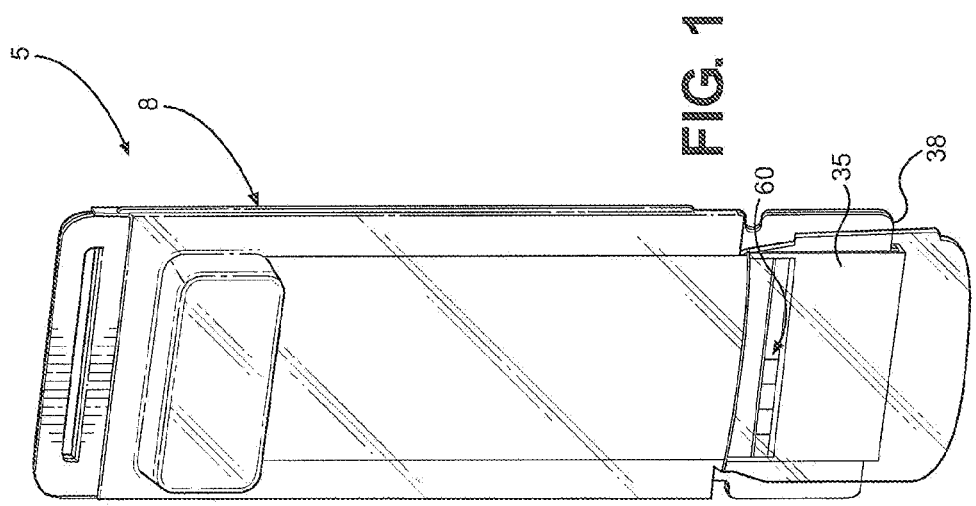

SYSTEM AND METHOD FOR OPTICAL DETECTION USING CAPILLARY ACTION

CROSS-REFERENCE TO RELATED APPLICATIONS

The present application is a continuation-in-part of and claims priority to International Application No. PCT/US2013/035121 entitled "System and Method for Optical Detection Using Capillary Action", filed Apr. 3, 2013, which claims the benefit of U.S. Provisional Patent Application Ser. No. 61/619,674 entitled "Optical Capillary Action Test Kit", filed Apr. 3, 2012, and U.S. Provisional Patent Application Ser. No. 61/718,345 entitled "Device and Method for Automated Optical Detection Using Capillary Action", filed Oct. 25, 2012.

BACKGROUND OF THE INVENTION

The present invention pertains to the field of analyte detection and, more specifically, to an automated system and method for the use of fluorimetric and colorimetric detection inks and capillary action to detect one or more target analytes, including explosives, narcotics, organophosphates, gunshot residue and toxic industrial chemicals.

The detection of small amounts of explosives is important for the prevention of terrorist attacks and for the safeguarding of civilians, military personnel and bases, airports and other transportation locations, and tourist and commercial venues. The low volatility of many explosives, such as TNT, RDX, and PETN, makes vapor sampling difficult and largely inefficient, especially at low temperatures. Thus, efficient solid-state sampling techniques are desirable for many applications. Chemical sensors are often desired because they are able to detect trace amounts of explosives and can be packaged into simple-to-use, low-cost devices. Conventional detection methods, such as X-ray diffraction, nuclear quadrupole resonance, and gas chromatography-mass spectrometry, though highly sensitive, are expensive, difficult to maintain, susceptible to false-positives, and are not easily manufactured into low power, portable devices. Low end systems, while physically simple compared to the high end systems, require more complex user interaction and interpretation.

A major source of terrorist funding is gained through narcotics trafficking. This relationship implies that there could be a correlation between narcotics and terrorist weapons, including explosives. Therefore, the ability to detect narcotics concurrently with explosives may potentially be valuable in fighting the terrorist network at large. In addition to the international needs, narcotics detection is also a focus for other domestic criminal and forensic applications. Narcotics of particular interest are heroin, cocaine, marijuana, and methamphetamines. Analytical instrumentation, such as FT-IR, Raman, GC-MS, and IMS, may be used to identify specific drugs, but these are typically ill-suited for widespread field use because of their size and/or expense. Existing colorimetric detection technology employed in presumptive forensic field-test kits is used to detect visible quantities of narcotics that are typically low milligram quantities. Many of these kits require sampling and dispensing an amount of one or more solutions into a reservoir, visually interpreting a color change, and referencing a color chart to look for a specific color while discounting other colors. This process can be time consuming, subject to bias in an individual's perception of color. The overall performance is subject to change based on an individual's eye sight and external lighting conditions. Automating the detection of these colorimetric kits would at least remove the subjectivity in detection and performance dependency on external lighting conditions.

Like narcotics, gunshot residue (GSR) is an important analyte of interest for both domestic and international operations. GSR is generated upon firing a weapon and is deposited on surfaces surrounding the weapon, including a hand of a shooter. GSR is produced from two sources: a primer and a propellant of the weapon's ammunition. The primer often contains heavy metal components, e.g., lead, barium and antimony, and the propellant usually contains nitrate-containing components, e.g., nitrocellulose. Criminal investigators can use GSR evidence in their work to determine many circumstances of a case, e.g., a firing distance and identity of the shooter. Identifying shooters is often done by collecting residue from the hand, either by dabbing the hand with adhesive stubs (which is relatively more efficient) or swiping with dry or wetting fabric/paper (which is relatively less efficient). The amount of residue deposited on the hand is small and dissipates over time and with activity, e.g., hand washing or wiping.

Currently, GSR can be detected in colorimetric presumptive tests or through a laboratory analysis. The presumptive tests usually focus on detection of propellant residue since there is more of it, and, therefore, the colorimetric signal is easier to observe visually. However, these tests are fraught with false positives, as nitrate-containing compounds are often found in the environment, e.g., fertilizers, food products, etc. Colorimetric tests for lead can also be used as presumptive tests, although the lead particles are so small that, oftentimes, the color produced is not visible to the naked eye. Analytical tests usually focus on primer residue and can determine the presence of the metal particles. Destructive tests such as atomic absorption simply identify, the presence of metals. Scanning electron microscopy (SEM) is the current gold standard in GSR detection because SEM can identify particles that are characteristic of GSR rather than simply identifying the presence of metals, which could be from other environmental sources, e.g., lead paint. Such characteristic particles contain all three of the main primer metals, i.e., lead, barium and antimony. Particle shape is also relevant to identifying the particles as being produced during the firing of a weapon. SEM can detect particles less than a micron in size and so has the advantage of detecting particles far smaller than those visible to the naked eye. However, SEM has the disadvantage of being expensive and time-consuming, with results often not being available to law enforcement for weeks or months.

A field presumptive test is of great value to law enforcement as it provides immediate, actionable intelligence for investigators. However, a confirmatory test is often needed to rule out environmental false positives and assist in any legal action against a suspect. Since the amount of GSR on a shooter's hand is small, efficient sample collection is vital. Running a field presumptive test can be problematic if the test is destructive (i.e., the GSR is consumed in the test and no longer available for a confirmatory test), as is often the case, especially with a nitrate-based test, which uses strong acids (e.g., >70% sulfuric acid, which destroys the characteristic GSR particles). Therefore, it would be advantageous to be able to collect a single sample that could be processed both in the field for a field presumptive test and subsequently in a confirmatory test.

A multi-assay tool capable of detecting explosives, narcotics, and GSR in a single instrument and correlating this data would be a valuable tool in combating terrorist and criminal activities, both domestically and internationally.

Optimization of such a tool for widespread use would require simplicity of use, portability, low power and maintenance requirements to be incorporated in a low cost device. Additional advantages would be gained by minimizing user interactions, particularly the number of analysis steps and ambiguity in user interpretation. Importantly, such an automated tool would allow for greater sensitivity and eliminated dependency on external lighting conditions and viewer's eyesight.

SUMMARY OF THE INVENTION

The present invention is directed to a product and method for the detection of one or more analytes in a collected sample, using capillary action in a sample card containing a sample substrate, which may have reagents embedded thereon, a test capsule containing a solvent reservoir and optionally containing detection reagents, and an absorbent pad that absorbs the contents of the test capsule and delivers the same to the sample substrate, and which may also have reagents embedded thereon, and a device which supplies one or more light sources, and records and processes the optical signal produced by the reaction between the detection reagents and the collected sample, and outputs a test result. The substrate may also contain a calibration signal to ensure the viability of the card and the validity of the test result. Additional aspects of the invention resides in the sample card itself, the use of the card with and without the reader device, visual analysis of the optical signal to determine a test result, and the specific form factor of the card itself.

A reader device includes a housing, a door, a card rupture mechanism, a light assembly, an optical reader, a signal processor and a communication system. The housing has a card carrier to receive the sample card, and the door is shiftably mounted relative to the housing and card carrier. The card rupture mechanism is configured to release the liquid in the test capsule after the sample card has been inserted into the card carrier and the door is closed. The optical reader is configured to read an optical signal produced by a reaction of the sample and the one or more detection reagents. The signal processor determines a test result based on the optical signal, and the communication system conveys the test result.

The present invention is directed more specifically to the detection of one or more of the following analytes: explosives, including nitroaromatic-, nitramine-, organic nitrate-, inorganic nitrate-, chlorate, perchlorate-, bromate-, and peroxide-based explosives; narcotics, including cocaine, heroin and other opiate drugs, marijuana, synthetic marijuana (e.g. K2, spice), PCP, LSD, GI-IB, Cathinones (bath salts), and methamphetamines (including salts and free-base forms of all narcotics); organophosphates; gunshot residue; and even toxic industrial chemicals.

The sample card may also contain a key, such as a bar code, color code graphic or notch in the housing, to indicate to the device which test (e.g. explosives versus narcotic) is being run to minimize possibility of operator error, and enable optimized analysis methods specific to the substance or class of substances for which the user is searching. In addition, the sample card may contain a unique identifier, such as a bar code serial number or area on which to write specific information, to assist in chain of evidence handling. The card may further contain a removable protective card cover over the sampling area to protect the reader device and sampling area from contamination before or after sampling, and to protect the user from touching the detection inks after the card has been processed.

Embodiments of the invention include the use of specific optical inks for the detection of explosives and narcotics. This includes their use in the present device, their use in the card component independent of the device, and other form factors. A test for PCP, methamphetamines, amphetamines, and cathinones, MDPV, mephedrone, mescaline, 2C-I and pyrovalerone, and their structurally related compounds and salts is disclosed which uses a pyrylium salt in an aqueous organic solution. A preferred embodiment of the methamphetamine and amphetamine test uses the ink on a substrate with a base, such as sodium hydrogen carbonate, sodium phosphate, sodium carbonate, or hydroxide salts contained thereon. A test for nitramine and organic and inorganic nitrates is also disclosed using a reducing agent and an organic amine in an acidic medium. A test for peroxide, chlorate, and bromate explosives is disclosed using an azino compound and an acid. A test for opiate-containing analytes using cis-aconitic anhydride is disclosed, preferably using an acid. A test for detecting and distinguishing between cocaine and PCP is disclosed, using both a cobalt(II) salt and a pyrylium salt, wherein the compounds may be distinguished based on the difference in color that results when the salts react with the drugs.

In one preferred embodiment, the system also includes an adhesive component for sample collection. The adhesive can be the sole area of sample collection, or a second sample may be collected onto it. The adhesive component is configured to couple to the sample substrate so that either 1) the samples can be combined to form a composite sample (in the case where both the sample substrate and the adhesive were used to collect separate samples), or 2) the adhesive is exposed to the detection reagents during the analysis. Preferably, the adhesive component includes a first adhesive portion, onto which the second sample is collected, and a second adhesive portion, which securely couples the adhesive component to the sample card. In one embodiment, the second adhesive portion contacts a rear portion of the sample card. The adhesive component can be separate from or integrated into the sample card.

In another preferred embodiment, after the test result has been determined in the reader device, the sample is analyzed using a second device that is distinct from the reader device. The second device is preferably a scanning electron microscope, though, the second device can also be a mass spectrometer or other analytical instrument that can yield specific chemical or physical information about the sample.

In one embodiment, a sample card preferably contains at least one of a surfactant and an acid. The surfactant aids in solvation of metal particles, skin oils and gun cleaning oils collected during sampling. The surfactant and acid can be individually located in at least one of the sample substrate, the liquid in the test capsule or the absorbent pad. Additionally, when an adhesive component is provided, the surfactant reduces a surface tension of the liquid to aid in wetting the adhesive component. Preferably, the surfactant is used in a sample card configured to detect GSR. However, the surfactant can also be used in sample cards configured to detect analytes other than GSR. When the analyte to be detected is GSR, the one or more detection reagents preferably includes a rhodizonate salt.

Additional objects, features and advantages of the invention will become more readily apparent from a detailed description of preferred embodiments thereof with reference to the drawings wherein like reference numerals refer to corresponding parts in the several views.

BRIEF DESCRIPTION OF THE DRAWINGS

FIG. 1 is a perspective view from one side of a sample card employed in the optical detection device of the invention;

FIG. 2 is a perspective view from another side of the sample card of FIG. 1;

DETAILED DESCRIPTION OF THE INVENTION

Detailed embodiments of the present invention are disclosed herein. However, it is to be understood that the disclosed embodiments are merely exemplary of the invention that may be embodied in various and alternative forms. The figures are not necessarily to scale, and some features may be exaggerated or minimized to show details of particular components. Therefore, specific structural and functional details disclosed herein are not to be interpreted as limiting, but merely as a representative basis for teaching one skilled in the art to variously employ the present invention.

The present invention is aimed at an analysis test for the detection of small amounts of analytes that may be present on a surface, which uses a liquid and capillary action to deliver reagents to a sample. In general, the test uses a sample card and a reader device. The sample card comprises a housing, a substrate for collection of a suspect material, one or more test capsules containing a liquid to react with the suspect material, and an absorbent pad to receive the liquid and to allow it to wick up the substrate in a controlled manner. The substrate and/or absorbent pad may optionally contain embedded reagents to react with the collected sample or liquid in the test capsule. A sample collection aid may optionally be used to acquire and/or transfer th suspect material more efficiently. The sample card contains an identifying mark, such as a bar code or notch in the housing, to indicate to the device the type of card being used. The reader device contains a housing with an input location (card carrier) to receive the sample card, a rupturing mechanism to break the test capsule, an internal light assembly to illuminate the sample and/or to initiate a reaction between the suspect material and reagents, solvent and/or solution, to produce an optical signal. The reader device also contains an optical reader to observe and record an optical signal, a signal processor to analyze the signal or recorded signal (a digital image of the signal) and determine a test result, and a means for communicating the test result to an operator.

Figure 3:
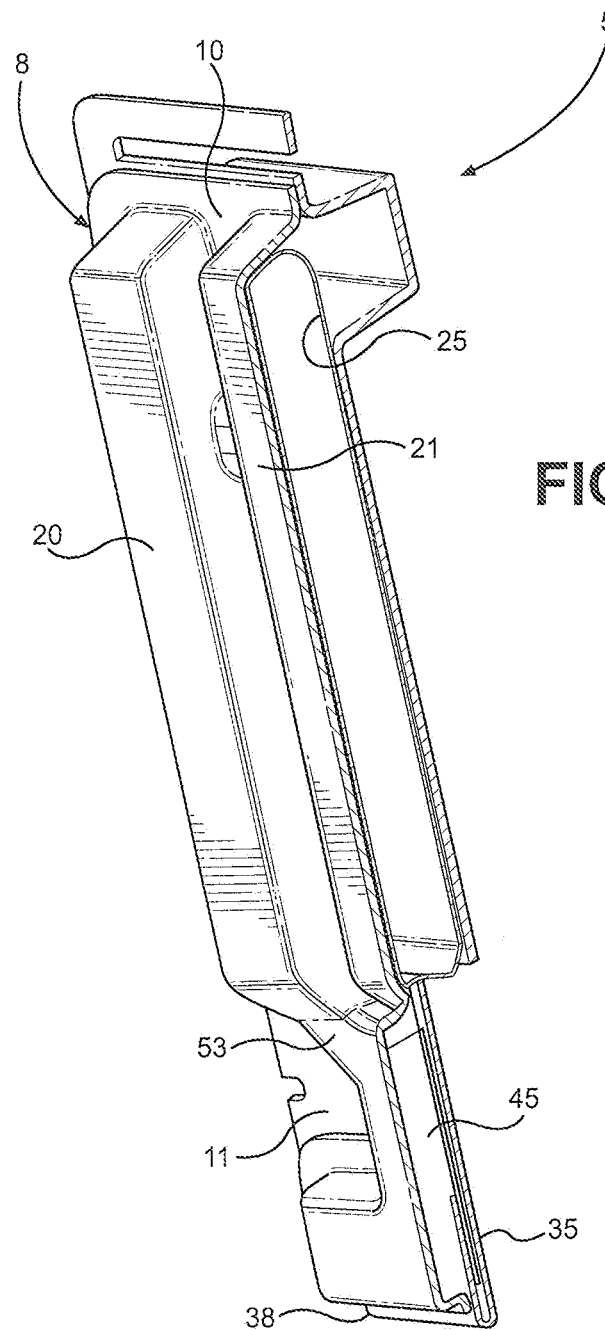
FIG. 3 presents a cross-sectional view of the sample card.

In describing exemplary embodiments of the invention, reference will initially be made to FIGS. 1-3 in describing the sample card which is generally indicated at 5. As illustrated, sample card 5 includes an outer covering or housing 8 which contains the other components of the sample card. Housing 8 includes an upper housing portion 10 and a lower housing portion 11. Housing 8 is preferably made of plastic or Teflon, but may be made of other materials. The housing 8 is formed with one or more cavities, with the illustrated embodiment depicting two such cavities 20 and 21, each of which is designed to hold a respective test capsule 25 shown in the form of an ampoule. Card 5 also holds a sample substrate 35, such as a paper substrate, for sample collection, with sample substrate 35 being shown exposed on or near a bottom edge 38 of sample card 5. Also provided as part of sample card 5 is an absorbent pad 45 which is positioned adjacent cavities 20 and 21 and juxtapose sample substrate 35.

Housing 8 is made of a flexible material which is compliant when pressure is applied. With this arrangement, as will be detailed more fully below, applying pressure to housing 8 at cavities 20 and 21 will cause the associated capsules 25 to burst such that liquid, e.g., a solvent with detection reagents, contained in the ampoules will be directed onto absorbent pad 45. In one embodiment, channels, such as shown at 53 and 54 in FIG. 2, can be formed as part of housing 8, with each channel leading from a respective cavity 20, 21. As shown, channels 53 and 54 merge at 55 above a reservoir 57. When multiple test capsules are employed, merging of the channels 53 and 54 allows solutions from the multiple cavities 20 and 21 to mix before coming into contact with or within the absorbent pad 45. This arrangement allows storage of incompatible solutions in the different capsules or ampoules 25, while accommodating mixing of the solutions to establish a testing solution prior to reaching the absorbent pad. In other embodiments, the solutions from the capsules 25 do not mix, but rather travel down to separate absorbent pads (not shown). In either case, from the absorbent pad 45, the testing solution wicks up the paper substrate 35 either along a common portion of the substrate 35 or along two different portions of the substrate 35. In the latter case, two detection tests can be run in distinct areas of the card to either test for two different materials, for false alarm mitigation, or to allow an internal calibration or control area.

At this point, it should be noted that the substrate 35 used to collect a sample of a suspect material allows the solution(s) contained in the capsules 25 to migrate along its surface and react with the sample, producing an optical signal. That is, each capsule 25 contains a solvent that is chosen and/or formulated to dissolve the suspect material and other detection reagents in the sample card 5 and facilitate a reaction between them to produce an optical signal, i.e. a fluorimetric or colorimetric signal. The substrate 35 may also contain embedded reagents that further react with the solvent/solution in the capsules and/or the suspect material. The substrate 35 may be cellulose paper, glass fiber paper, cotton paper, or other material such as a cloth or muslin material that acts as a wick to absorb the solution and allow capillary action to draw the solution up the length of the substrate 35. In the embodiment shown, the paper wraps around the front of sample card 5. One end of the paper is placed between the housing 8 and the absorbent pad 45, and folded around the front of the housing 8. The paper may be held down by an adhesive label (shown without a reference numeral), which may also contain marketing and/or other information as to which analytes may be detected with the particular sample card 5. The exposed portion of the paper is the sample collection area. Swiping or dragging the paper along a surface is a convenient method of collecting a sample. Once the liquid is released from the capsule(s) 25, it will dissolve any reagents embedded on the absorbent pad 45 and substrate 35 and wick along the substrate 35. Therefore, a wicking material and capillary action is employed to deliver a liquid to a test area and create an optical signal, usually a colorimetric signal, to indicate the presence of a specific analyte. The simplicity of this design approach is useful for determining the presence of compounds that require a single detection solution, or can be performed in a single step by carrying solution to a solid reagent embedded in the solvent wicking pathway. The arrangement is considered particularly useful when solid particulates must be extracted from a sample to avoid interference in the detection signal.

In any case, as the solution passes through the sample, the target analyte is dissolved and carried along the length of the substrate 35, and produces an optical signal. Users may be directed to sampling on the bottom edge so that as the ink (solution) passes over the substrate, dirt and other large particles are left at the bottom of the sample collection area and are positioned such that they can be removed or otherwise excluded from the signal processing. A sample collection aide may also be used in conjunction with the sample card 5 to make sampling from certain surfaces more efficient. For example, a cotton swab may be used to collect a sample from the inside of a small bag and then rubbed on the sample collection area of the paper. In other embodiments, the substrate preferably has a portion which is not used for sample collection and serves as a control area. This portion may contain a small amount of material which will generate the target signal to assist signal processing and to ensure that each card is performing properly.

The sample card 5 may also be designed with an identifying indicator or mark 60, such as in the form of a mechanical key, bar code, notch or other physical or graphical component, located on the housing 8, the substrate 35, or a label (not shown) affixed to sample card 5. Identifying indicator 60 functions to specify the type of sample card 5 and, correspondingly, the solution/substrate contained therein such that the appropriate sample card 5 can be employed for a given test, e.g., a cocaine test vs. a homemade explosive test. The identifying indicator 60 can be employed for visual identification with the human eye, or recognized by an optical reader or camera. In any event, the identifying indicator 60 correlates with the type of test being performed. In certain embodiments of the invention, the inclusion of the identifying indicator 60 allows the overall system to automatically determine and perform the desired testing with the appropriate sensing algorithms, processing and analysis. Sample card 5 may also have an area on which to write notes to allow sample card 5 to be used for evidentiary purposes.

Figure 4:
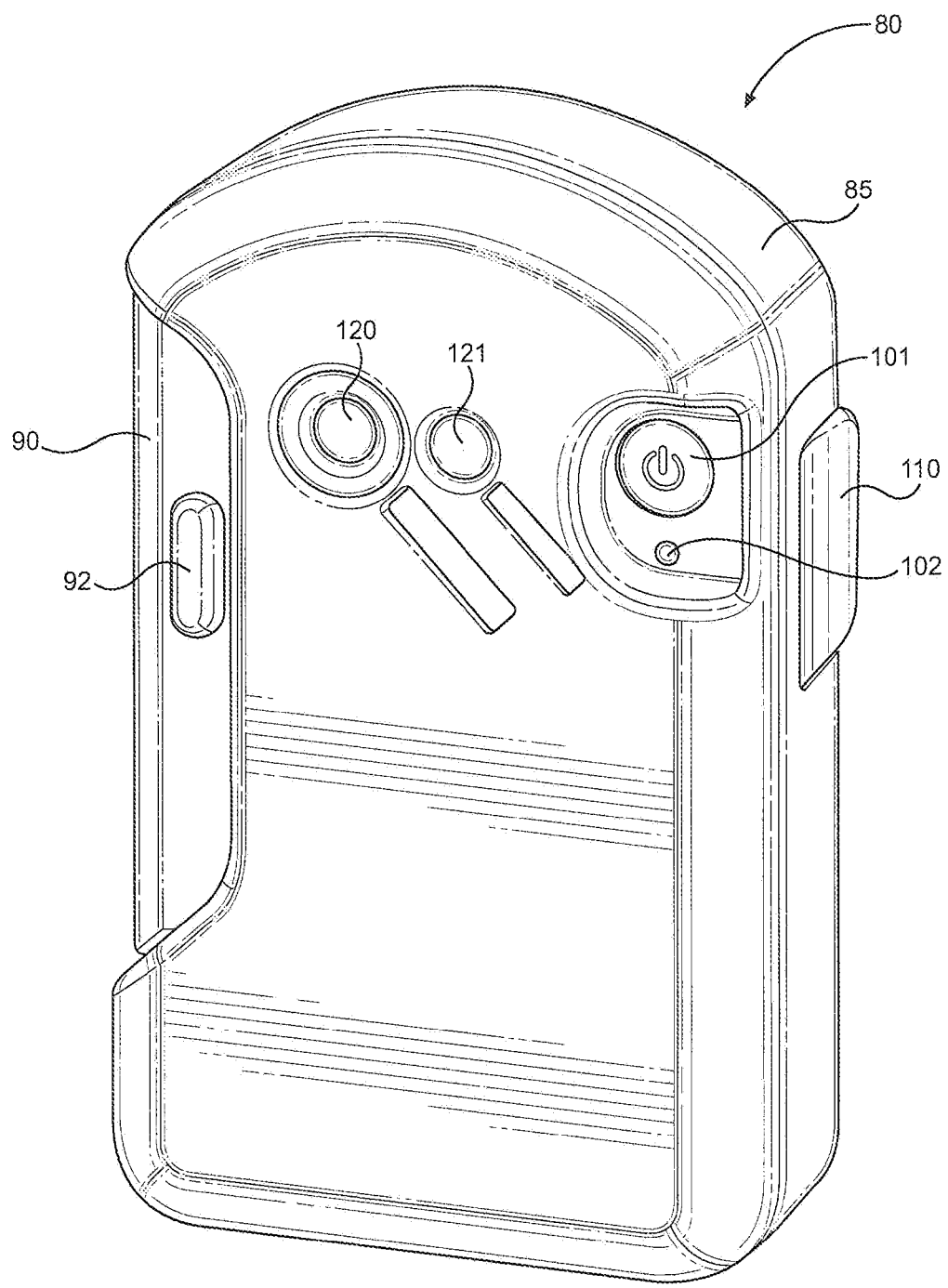
FIG. 4 is a perspective view of a reader of the optical detection device shown in a closed condition.

In accordance with the invention, sample card 5 may be used independently, with the optical signal being observed visually by the user to determine a test result. More preferably, the card 5 is used in conjunction with, a reader device 80 to determine the test results automatically, as will now be detailed. with reference to FIGS. 4-6. As shown, reader device 80 includes a main housing 85 having a door 90 which can be pivoted or otherwise shifted between opened and closed positions, with the opened position being achieved through activation of a release button 92. Reader device 80 also includes a power button 101 and an activation and/or low battery indicator light 102. Also shown provided on a side of main housing 85 is a port cover 110, such as a rubber insert, which can be selectively removed to expose an area for connecting reader device 80 to an electrical outlet for charging purposes, connecting reader device 80 to a computer via USB or other communication port for data storage/transfer and firmware upgrading purposes, and inserting/removing a memory card (not shown). Furthermore, reader device 80 includes one or more communication ports, such as indicated at 120 and 121. In this embodiment depicted, each communication port 120, 121 contains an LED light, e.g., a green light and a red light, used to respectively convey positive and negative results of a given test.

Figure 5:
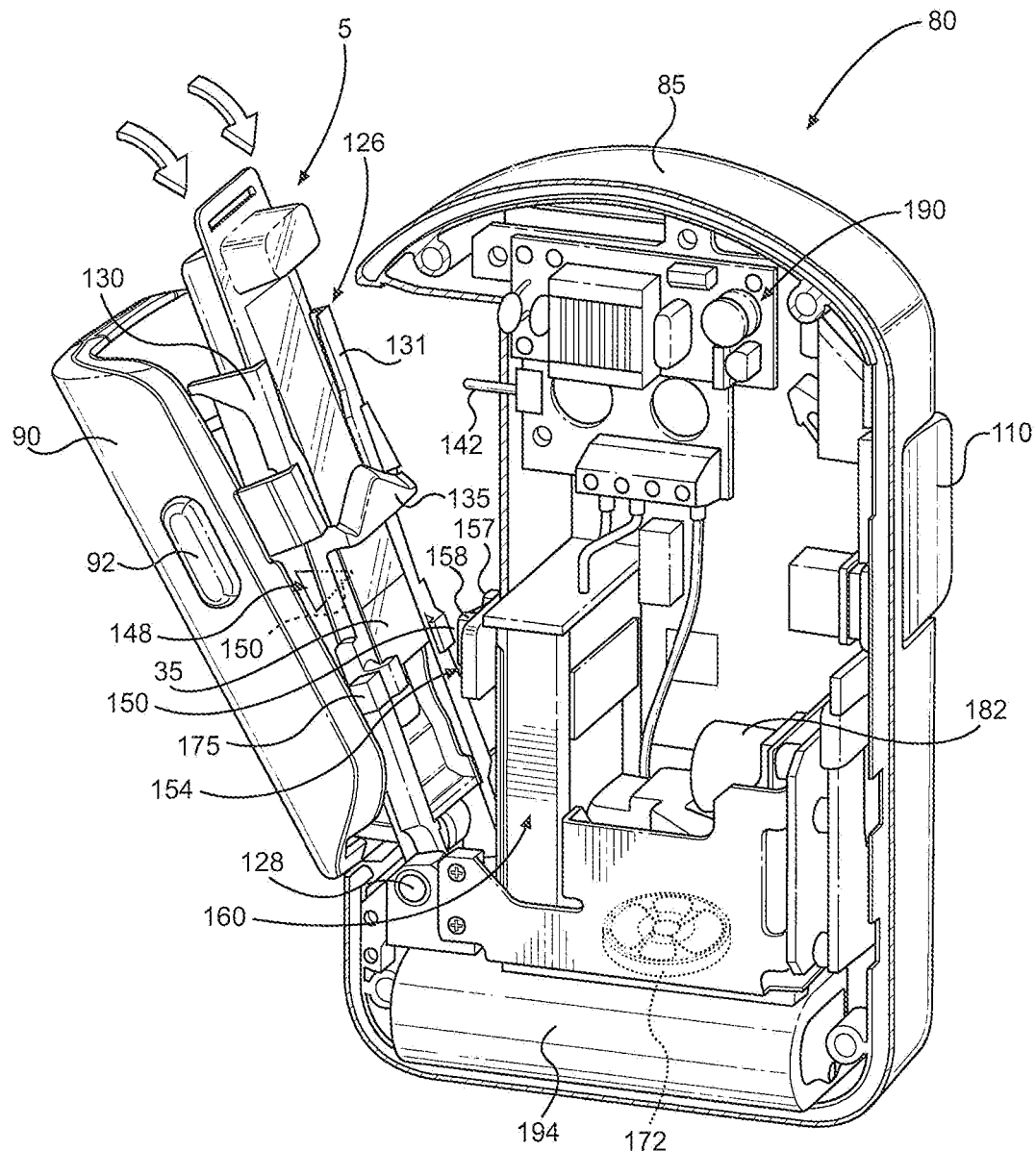
FIG. 5 illustrates the reader of FIG. 4 in an open condition and with internal components being depicted.
Figure 6:
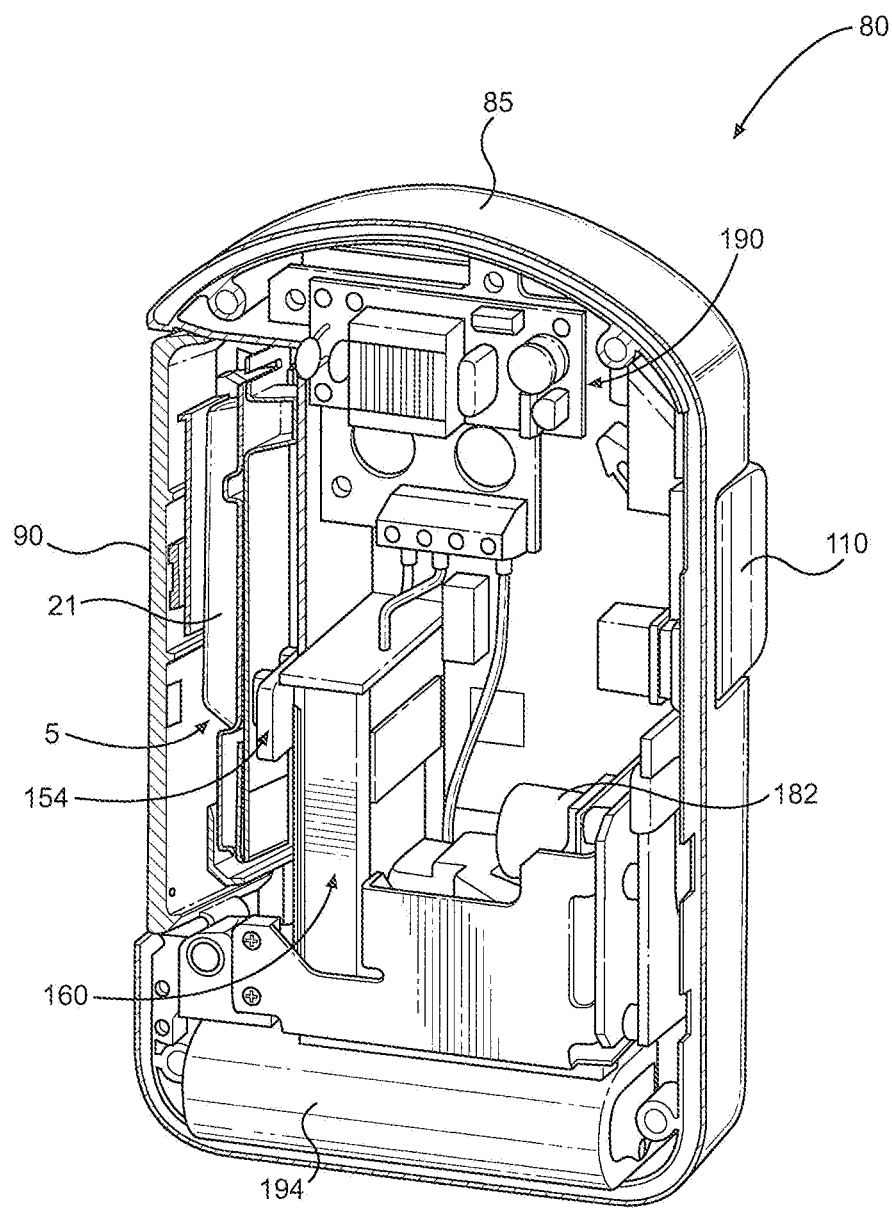
FIG. 6 is a view similar to FIG. 5 but with the device in the closed condition.

Reader device 80 also includes various internal components as shown best in FIGS. 5 and 6. More specifically, reader device 80 has a card carrier 126 into which the sample card 5 is placed for testing purposes. The card carrier 126 is shown extending into an inside portion of door 90 and is separately, pivotally connected to main housing 85 for movement about a pivot axis 128, but could take other forms, such as a slot or a sleeve that is exposed when a door is opened. As illustrated, card carrier 126 includes side guide channel members 130 and 131 which are interconnected by a crosspiece 135. Sample card 5 is configured to fit between side guide channel members 130 and 131, and behind crosspiece 135. Proper positioning of sample card 5 contributes in minimizing cross-contamination between the sample collection area and the reader device 80. With this arrangement, when door 90 is opened, the card carrier 126 pivots out as shown in FIGS. 5 and 6 so that card carrier 126 is readily accessible by an operator for inserting or removing of sample card 5. The reader device 80 may contain a card sensor, which senses when a sample card 5 is fully engaged in card carrier 126. The device may also contain a door sensor, which senses when door 90 is fully closed. Preferably, the card and door sensors is constituted by a single mechanical switch 142 which senses when both a sample card 5 is inserted in card carrier 126 and door 90 is closed. Preferably, a detection cycle is automatically started when the sensor 142 determines the sample card 5 has been inserted and the door 90 has been subsequently placed in the closed position which, in the embodiment shown, also constitutes pivoting door 90 about axis 128. If door 90 is open during a detection cycle, the system would abort the current detection process, such as to assure an accurate analysis and to protect the user.

The reader device contains a rupture mechanism generally indicated at 148. Basically, rupture mechanism 148 functions to rupture the capsules 25 or otherwise releases their liquid, typically by applying pressure to or puncturing the capsules. Pressure can cause glass or plastic ampoules to break, or a plastic pouch. to burst and release its contents. In the depicted embodiment, door 90 on main housing 85 is provided with a protrusion 150 which extends into the card carrier 126 when door 90 is closed. More specifically, main housing 85 has mounted therein an anvil member 154 which is shown to include two support blocks 157 and 158 which align with cavities 20 and 21. When door 90 is closed, cavities 20 and 21 are limited in movement based on the presence of blocks 157 and 158 while protrusion 150 pushes against capsules 25, thereby rupturing capsules 25 and releasing their contents. When the door 90 is opened, the protrusion 150 is pulled out from the card carrier 126, allowing one sample card 5 to be removed and another inserted and fully coupled to card carrier 126. Another embodiment allows two or more capsules to be broken at different times, thus allowing a time-release or multiple-ink detection process to take place. Once the contents are released, they funnel down to the absorbent pad 45. Upon wetting, the solution is drawn from absorbent pad 45 to and along the substrate 35 through capillary action. It passes through the sample collection area and the collected sample.

Reader device 80 can also have a means to sense indicator 60 to determine the specific analyte or group of analytes of interest for which the sample card 5 has been designed. Reader device 80 can therefore execute a predetermined protocol specific to the individual sample card 5. For example, different lighting and signal processing, heating and drying cycles may be used for nitroaromatic explosives than for specific narcotics. As referenced above, this sensing may be done by reading and analyzing various different indicators, including a bar code, color code graphic, or other printed graphical code on the label or a physical key on sample card 5.

The reader device 80 also contains a light assembly 160, which may serve multiple purposes. In particular, light assembly 160 illuminates the sample such that an optical reader (discussed further below) can determine the sample card type (e.g., by illuminating the identifying mark 60), verify the status of the solvent flow (e.g. ensure the sample card 5 is not defective), and read the optical signal caused by the interaction of the solution and the collected sample. The light assembly 160 may also further serve to initiate or stimulate a reaction. The light assembly 160 may be comprised of one or more light sources, including white light, UV light, and infrared light. This may be supplied by light emitting diodes (LEDs), cold cathode fluorescent lamps (CCFLs), or hot cathode fluorescent lamps (HCFLs). The light assembly 160 also illuminates an optical signal. For colorimetric signals in the visible spectrum, white light may be used; for fluorimetric signals, UVA or UVB light may be shone onto the sample to stimulate the optical signal. There may also be a portion of the substrate 35 that is not exposed to the suspect material which serves as a control. This portion of the substrate 35 will show an optical signal from the solution itself as it would appear if it had not come into contact with the target material for which it was formulated to detect.

Reader device 80 may optionally include a fan 172 to help dry the solvent from the viewing area if necessary. The reader device 80 may also include a heater 175 to aid in drying or to stimulate a reaction between the sample and solution, depending on the specific chemistry related to the card. The convection flow or heat may be triggered automatically when reader device 80 senses the solvent front has reached a specific point in the viewing window. In another manner, the function of the convection flow and heat may be controlled in a time sequence after initiation of a detection process based on the individual card type.

Reader device also contains an optical reader 182 to observe and record an optical signal from the substrate 35, i.e., both the portion which is exposed to the sample, and the control area, if included. Optical reader 182 can take various forms, but preferably takes the form of a simple camera or spectroscopic reader. Preferably, optical reader 182 records a digital image of the sample collection area and the optical signal. Furthermore, several images may be captured and recorded in a timed sequence and analyzed for changes in the optical signal from one image to the next, thereby identifying and incorporating attributes that evolve over time, and allowing a test result to be determined as soon as possible to minimize overall detection time.

Reader device 80 further contains a signal processor or controller 190 which is powered by a rechargeable battery 194 and has the capability to aggregate data from multiple sensor inputs and determine a test result. Various inputs can be collected, including temperature and humidity signals from sensors (not shown) within housing 85. More specifically, controller 190 includes an image processing capability to assess the optical signal as recorded in a digital image from the processed sample for the presence of the target analyte. The image processing may include preprocessing such as the collection of a preprocessed image, masking of preexisting signals, and normalization. In the preferred embodiment, the image processing includes multiple orthogonal attributes of the optical signal to produce a robust and reliable assessment. The assessment attributes may include color component identification and/or separation, signal energy levels, relationships between color components, time domain appearance and disappearance of signals, signal shape, and signal distinction. Color component identification may include pre-determined acceptable color component range variations for each component (e.g. red-blue-green (RGB) components or hue-saturation-brightness (HSB) components), and a logical test to determine if the interrogated color point falls within the acceptable range variations for each component. In one embodiment, a control signal may be embedded and processed on the same sample card 5 used to collect the suspect material. In another embodiment, the control signal may be collected in advance and independent of the sample collection and analysis process. In addition to the digital image, additional sensor inputs evaluated by the signal processing capability may include temperature and humidity measurements, which may affect the parameters by which the optical signal is assessed. The extracted assessment attributes are compared to the control signals and an overall assessment regarding the presence of the target analyte is made (i.e. the unit determines a test result).

For sample cards that have two capsules whose contents do not mix before reaching a sample paper, but rather travel side-by-side to the sample collection area, the signal processing compares the two optical signals to determine the test result. This may be used as a means to mitigate false alarm or to improve the specificity of the test. For instance, one capsule may be used to test for the presence of either cocaine or PCP while the other side would test for PCP only. If both sides produce a positive signal, the signal processor would determine a positive test result for PCP; if only one side produces a positive signal, the device would determine a positive test result for cocaine.

The test result is communicated to the user through a communication system, such as by providing an indication of either a 'detection' or 'not a detection'. Preferably, the communication system may also communicate an error to the user. Such instances warranting an error message would be to indicate a defective card (e.g. no solvent front was detected after an analysis started) and to indicate a card not supported by the unit's currently installed firmware is present (e.g. the unit was unable to read the unique identifying mark). The communication system may include LEDs, an LCD display, or other audio, visual or vibration cues to the user regarding the status of the device and the test result. In one embodiment, two LEDs are provided at communication ports 120 and 121 as detection indicators to indicate a positive detection or no detection. Preferably, multi-colored LEDs are used such that error messages may be communicated through different colors than the detection/no detection colors. In another embodiment, an LCD display may give textual and/or pictorial commands.

Preferably, reader device 80 further contains data storage and communications capabilities. That is, the images captured from optical reader 182 may be stored, as can intermediate results and final results from the optical signal analysis. This stored information may be communicated to the user for collection and storage with other forensic elements of the detection event. Reader device 80 may further support remote or local connectivity to allow data transfer.

Figure 7:
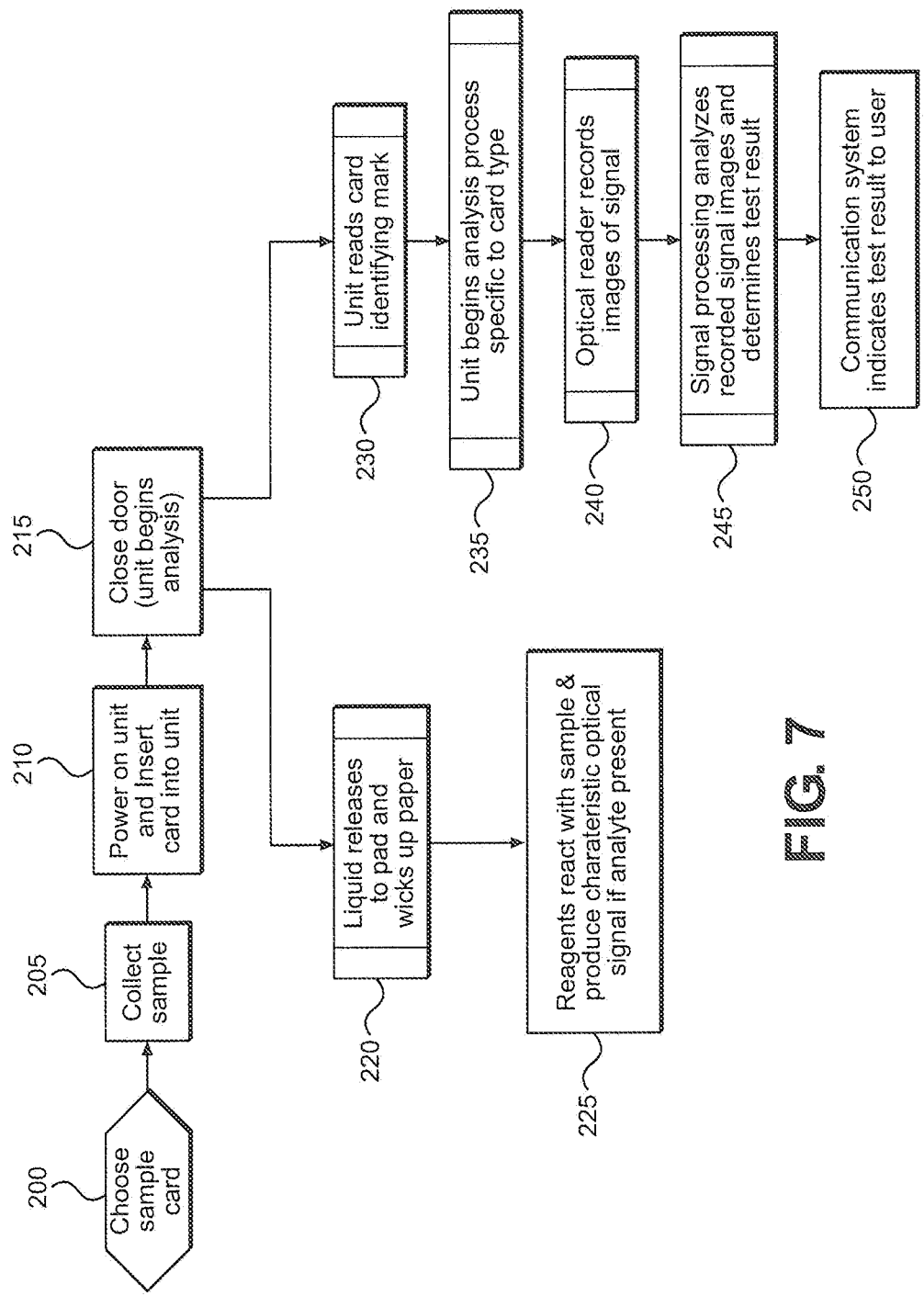
FIG. 7 is a flow chart outlining method aspects of the invention.

Reference will now be made to FIG. 7 in describing a typical analysis in accordance with the invention, with the typical analysis including a sample collection with sample card 5 and then analysis in reader device 80. First, an operator finds a sample to be tested. This may be a suspect powder (e.g. for a drug analysis), a suspect's hands (e.g. to determine if the suspect recently fired a weapon or has handled explosives), or other surface. The operator locates the correct sample card 5, specific to the analyte (e.g. heroin) or class of analytes (e.g. opiates) for the desired test as indicated at step 200. The surface on which the sample is present is then swiped at 205 with the sample collection area, or a cotton swab or other sample collection aide is wiped across the surface and the sample is then transferred onto the sample collection area. At step 210, the power to reader device 80 is turned on, door 90 is opened, and the sample card 5 is placed in card carrier 126, thereby coupling the sample card 5 to reader device 80. The door 90 is shut at 215, with one or more sensors 142 verifying that sample card 5 is present and door 90 is shut. With the shutting of door 90 on card 5, rupture mechanism 148 is engaged, causing capsules 25 to release their contents and the solvent to wick up the substrate 35 at step 220. As the liquid is released at 220 and the reagents react with the collected sample at 225, reader device 80 also begins to automatically initiate a detection cycle, including beginning with the system turning on white light to read an identifying mark on the card to determine which card is present at 230. The contents of the capsules 25 flow down the channels 53 and 54 to the absorbent pad 45. The absorbent pad 45 is in contact with the substrate 35, and allows the liquid to wick along the substrate 35 in a controlled manner through capillary action, which is in contact with the absorbent pad 45. If reagents are present on the pad or paper, the solvent dissolves them and carries them up the paper as well. The solution mixes with and reacts with the collected sample (step 225). White light is turned on and an optical reader 182 senses the presence of the solvent front and continues analysis (note, if no solvent was detected the system would return an error indicating a defective card). The system then optionally triggers, depending on a program defined by the specific sample card used, activation of drying fan 172 and/or heater 175 to dry the surface and potentially supply energy to increase the reaction rate. Lights are turned on, again specific to the individual sample card 5 used (step 235), and optical reader 182 records an optical signal (step 240). Signal processing system 190 analyzes the optical signal against a control area on the sample card and/or to pre-programmed color sets specific for the individual sample card 5. The signal processing system 190 determines a test result (step 245) and communicates it to the user (step 250) by lighting an LED to indicate the presence or absence of the suspect material.

The system described above holds significant advantages over current colorimetric detection technology available. For instance, the system provides magnification and high resolution, allowing for enhanced sensitivity, and need not be dependent upon an operator's eyesight or varying lighting conditions. It provides consistent interpretation of the detection result not based on personal bias, color variation, or perceptions of a user. The housing of the reader device chamber minimizes contamination, provides a controlled environment for the chemicals (e.g. temp, moisture, heating, drying) and increases safety. The automated system further allows the user to focus on his/her primary duty and provides detection consistency and accuracy that makes it suitable for presumptive tests used in legal cases.

In further accordance with the invention, there have been developed particular inks for use as the detection reagents for specified analytes. To this end, a new optical test solution for PCP, methamphetamines, amphetamines, and "bath salts" using a pyrylium salt is disclosed. This solution may be used in multiple form factors, including in the sample card disclosed herein. An optimal solution uses triphenylpyrylium tetrafluoroborate in an acetone: water mixture. Amphetamines, methamphetamines and their structurally-related compounds turn yellow or orange when exposed to this ink. PCP turns red or violet-red when exposed to this ink. To increase the sensitivity to the hydrochloride salts of the methamphetamines and amphetamines, a base may be added to the substrate or to the solution. The base deprotonates the narcotics, which allows them to react with the pyrylium reagent more efficiently. Useful bases include hydroxides, carbonates, phosphates, and bicarbonates. In a preferred embodiment, a PCP sample card uses a standard paper that has not been exposed to base. In a preferred embodiment, an amphetamines (and related compounds) sample card will test for the free-base and protonated forms, and will use a paper or absorbent pad that has been coated with a sodium bicarbonate prior to manufacturing of the sample card. Removing the base from the pyrylium solution, in the test capsule improves stability of the solution. The yellow-orange to orange-red color produced by the reaction may be observed visually or in an automated system, such as the reader device described above.

In connection with an optical test for nitramines (e.g. RDX, HMX, C4), organic nitrates (e.g. PETN, Semtex, EGDN, nitrocellulose, nitroglycerin), and inorganic nitrates (e.g. ammonium nitrate, ANFO, urea nitrate, potassium nitrate, sodium nitrate), the detection reagents includes an acid, one or more organic amines, and a reducing agent. Preferably, the reducing agent is separated from the other compounds to ensure the stability of all compounds. In a preferred embodiment, a sample collection paper contains a reducing agent, preferably zinc dust, thereon. The paper is used to collect a sample and then exposed to an organic solution containing an acid, preferably hydrochloric acid, and one or more organic amines, and preferably at least N-(1-naphthyl)ethylenediamine. The reaction produces a strong pink color in the presence of these nitro-containing compounds. The pink color may be observed visually or in an automated system, such as the reader device described above.

A particular optical test for peroxide-, chlorate-, and bromate-containing compounds, including explosive-related compounds, is disclosed that uses an azino compound in an organic solvent containing an acid. Preferably, 2,2'-azinobis(3-ethylbenzothiazoline-6-sulfonic acid) is used in a solution of ethanol and hydrochloric acid. Heat may be used to increase the reaction rate and efficiency. The reaction produces a green compound, which may be observed visually or instrumentally, such as with the reader device described above.

In an optical test for the detection of opiate compounds and cocaine, cis-aconitic anhydride in an organic solvent containing an acid, preferably acetic acid, is employed as the detection reagent. The reaction produces a yellow colored compound which may be observed visually or instrumentally, such as with the reader device described above.

An optical test for the detection and discrimination between cocaine and PCP is disclosed which uses a cobalt (II) salt and a pyrylium salt. Cobalt(II) compounds, particularly cobalt(II) thiocyanate, or Scott's reagent has long been used to detect cocaine through production of a blue compound. PCP is also detected with this reagent, though typically PCP has been described as a nuisance alarm for the tests marketed for cocaine detection. Addition of a pyrylium salt, preferably triphenylpyrylium tetrafluoroborate, causes the colored product of the PCP-product to shift from the typical blue color to a more green color. Thus, for a mixture of Scott's reagent and the pyrylium compound reacting with an unknown substance, cocaine can be assumed to be the analyte present if a blue color is observed, while PCP can be assumed to be the analyte present if a green color is observed. The color change and discrimination between the drugs may be observed visually or instrumentally, such as with the reader device described above.

A presumptive GSR detection field test is disclosed, which is based on a sodium rhodizonate test for lead. Afterwards, the sample can be analyzed with an analytical technique, such as SEM, to confirm the presence of specific metals or characteristic GSR particles. In this embodiment, sample card 5 is modified to enhance sample collection efficiency, as shown in FIG. 8. Specifically, sample card 5 includes a sampling adhesive, either separate from or integrated directly into sample card 5. In one embodiment, a user collects a sample, first by dabbing a surface of interest (e.g., a suspect's hand) with an adhesive component 300, and then, optionally, swiping the surface with sample substrate 35. To prepare the sample for analysis, adhesive component 300 is applied over the top of sample substrate 35 and then adhesive component 300 and sample substrate 35 are pressed together, thus combining the two collected samples into a single sample, or, if only one sample was collected onto the adhesive, preparing the adhesive for proper analysis. To prevent adhesive component 300 from detaching or lifting from sample substrate 35 during sample analysis (e.g., when the paper is wetted with a liquid), adhesive component 300 can optionally be adhered to sample card 5 with additional adhesive that wraps around sample card 5.

Figure 8A:
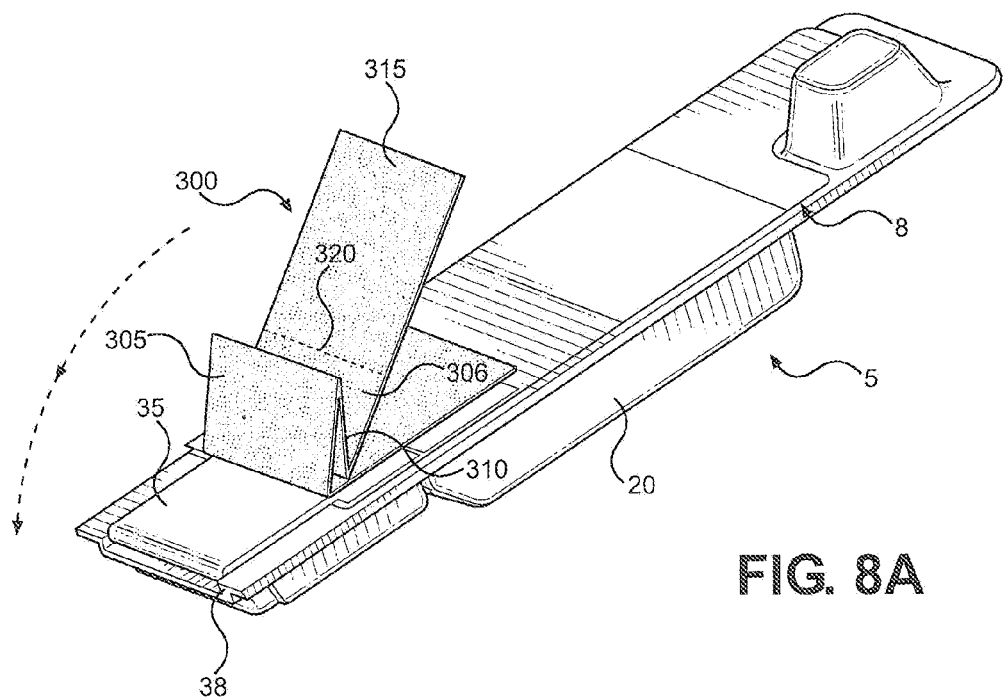
FIG. 8A is a perspective view of the sample card with an adhesive component in accordance with the present invention.
Figure 8B:
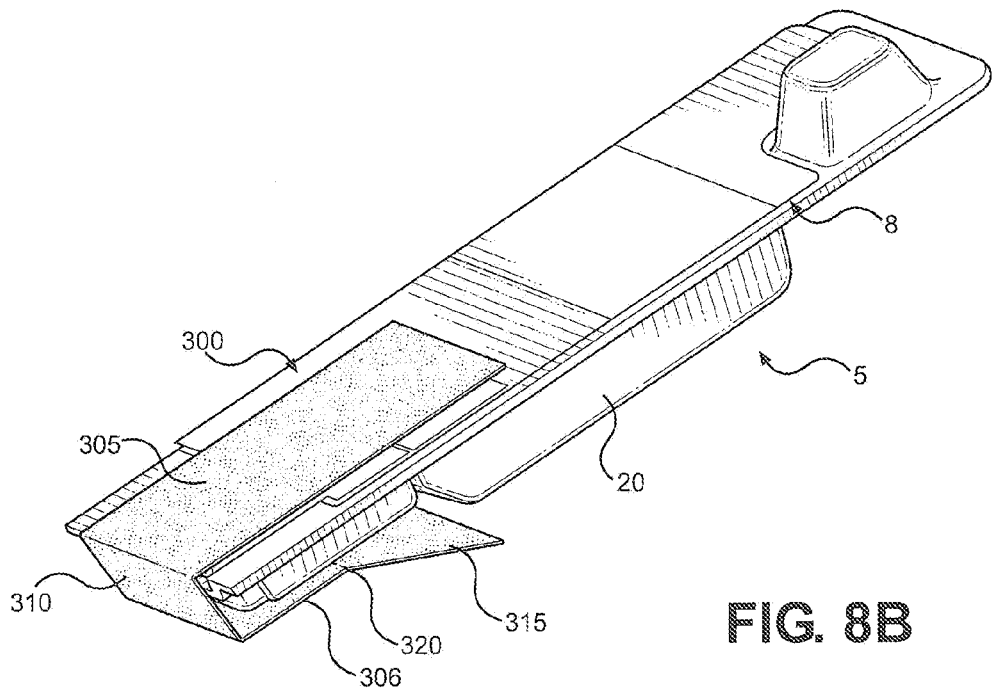
FIG. 8B is a perspective view of the sample card and adhesive component of FIG. 8A showing the adhesive component in a second position.

In the embodiment shown in FIGS. 8A-B, adhesive component 300 is integrated into sample card 5 by being coupled thereto. Adhesive component 300 includes two adhesive portions 305, 306; hinge portion 310; a pull tab 315; and a tear line 320. Adhesive portion 305 represents the area of adhesive component 300 that is touched to the surface of interest and then pressed to sample substrate 35. Adhesive portion 306 is coupled to adhesive portion 305 through hinge portion 310 such that adhesive portion 306 can be wrapped around bottom edge 38 of sample card 5 and adhered to the rear of sample card 5. Preferably, adhesive component 300 initially lays flat against sample card 5. After the user collects the sample using adhesive portion 305 and, optionally, the sample substrate 35, the user uses pull tab 315 to pull adhesive component 300 away from sample card 5 and wrap adhesive component 300 around bottom edge 38 such that adhesive portion 305 contacts sample substrate 35 and adhesive portion 306 contacts the rear of sample card 5, as shown in FIG. 8B. Optionally, pull tab 315 is then separated from the remainder of adhesive component 300 along tear line 320.

Figure 9A:
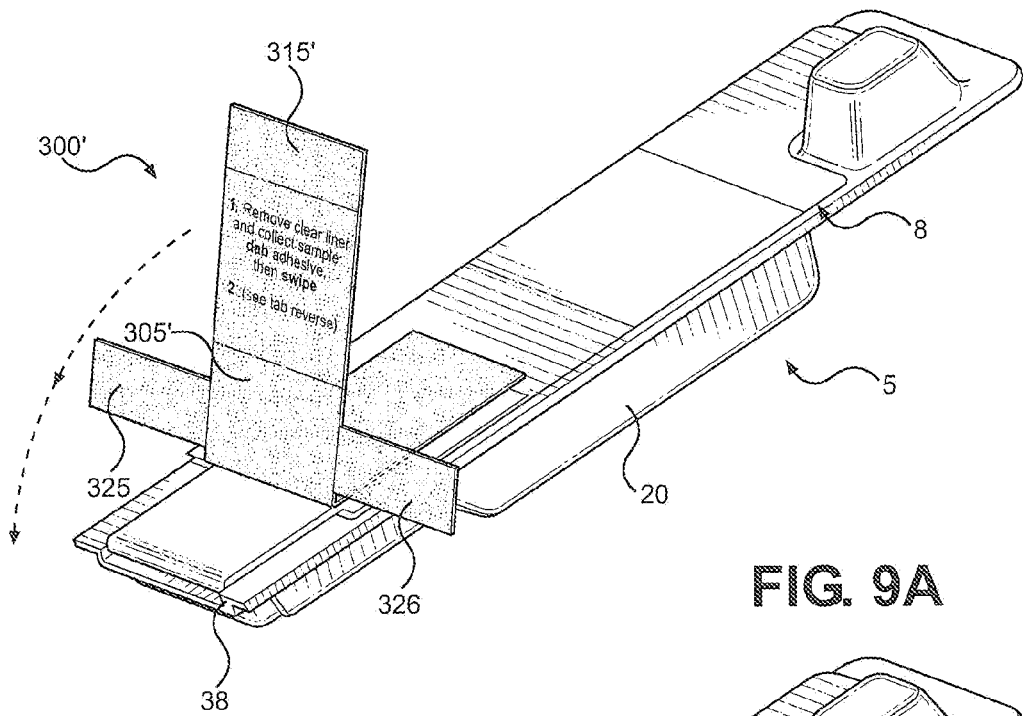
FIG. 9A is a perspective view of the sample card with an adhesive component according to a second embodiment of the present invention.
Figure 9B:
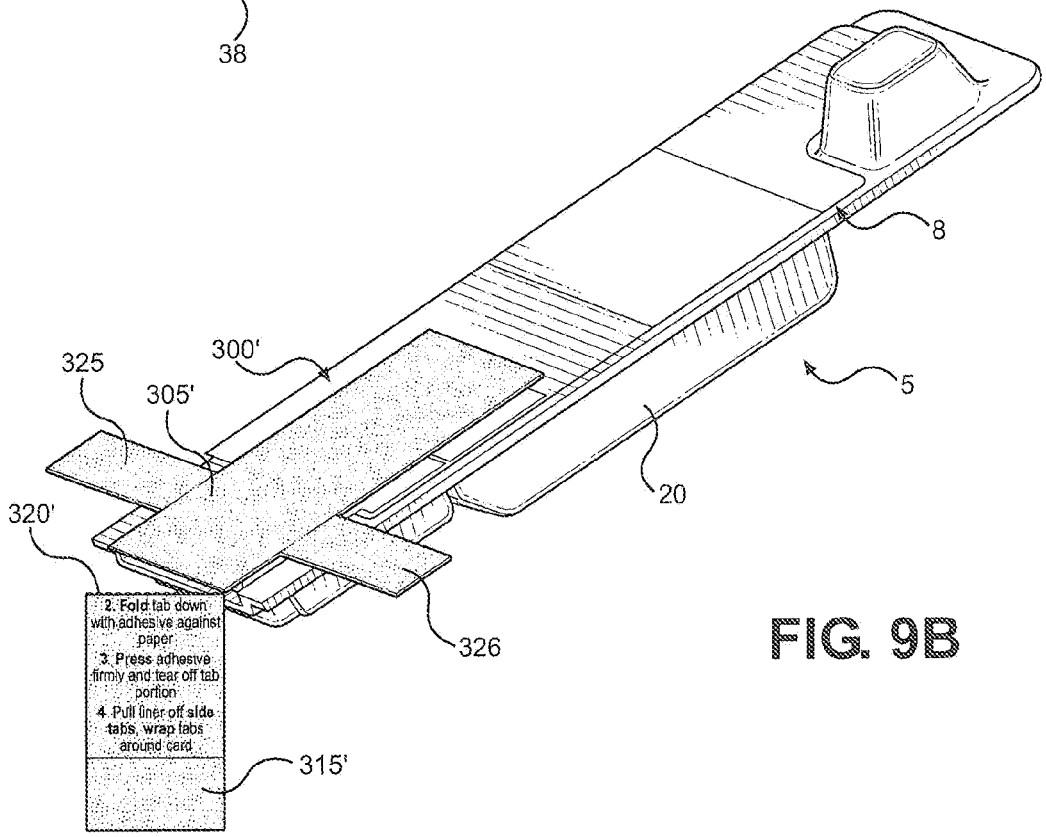
FIG. 9B is a perspective view of the sample card and adhesive component of FIG. 9A showing the adhesive component in a second position.
Figure 9C:
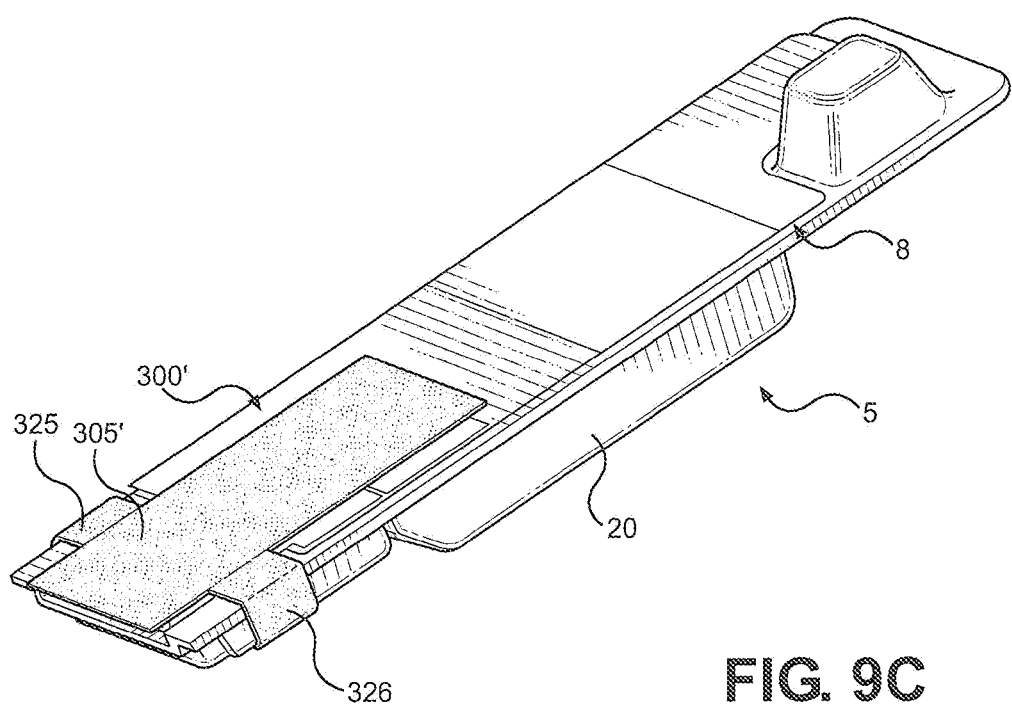
FIG. 9C is a perspective view of the sample card and adhesive component of FIGS. 9A and B showing the adhesive component in a third position.

In an alternative embodiment shown in FIGS. 9A-B, an adhesive component 300' includes an adhesive portion 305'; a pull tab 315'; a tear line 320'; and two side tabs 325, 326. As with adhesive component 300, adhesive portion 305' represents the area of adhesive component 300' that is touched to the surface of interest and then pressed to sample substrate 35. Preferably, adhesive component 300' initially lays flat against sample card 5. After the user collects the sample using adhesive portion 305' and, optionally, the sample substrate 35, the user pivots adhesive component 300' away from sample card 5 using pull tab 315' until adhesive portion 305' contacts sample substrate 35, as shown in FIG. 9B. Pull tab 315' is then separated from the remainder of adhesive component 300' along tear line 320'. Next, an adhesive on each of side tabs 325, 326 is exposed, and side tabs 325, 326 are wrapped around and adhered to the rear of sample card 5.

Although described with reference to two particular embodiments, it should be understood that the sampling adhesive can be provided in a variety of different ways. As discussed above, in addition to adhesive component 300 being integrated into sample card 5, adhesive component 300 can be formed separately from sample card 5 and then coupled thereto immediately prior to analysis (e.g., by pressing adhesive component 300 to sample substrate 35 and then adhering adhesive component 300 to sample card in some manner). Also, adhesive components 300, 300' can be constructed in numerous ways.

For GSR use, one form of sample card 5 includes a rhodizonate salt (e.g., sodium rhodizonate or potassium rhodizonate) in conjunction with water or aqueous solution as a test liquid. Ideally, the rhodizonate salt is separated from the solution for extended shelf life. In a preferred embodiment, the test liquid contains an acid and a surfactant, though, in some embodiments, only one is used. The acid aids in oxidation of some of the elemental lead that may be present. The surfactant serves multiple purposes. First, the surfactant aids in solvation of the metal particles within the aqueous liquid, thus allowing it to react more efficiently with the rhodizonate. Second, the surfactant helps to solvate any skin oils, gun cleaning oils or other organics that were collected from the surface of interest (e.g., a suspect's hand) that may coat or inhibit reaction of the lead with the rhodizonate. Third, the surfactant reduces the surface tension of the water and thereby aids in the solution wetting the sampling adhesive (i.e., adhesive portion 305 of adhesive component 300) to bring the metal particles from the adhesive into the reaction matrix. Each of the rhodizonate salt, the surfactant and the acid can be located in any one of test capsule 25, sample substrate 35 or absorbent pad 45.

Sample card 5 can be analyzed visually to observe a characteristic colorimetric reaction product to presumptively identify lead (a component of many primers). Since the primer particles are generally too small to be observed visually, analyzing sample card 5 in reader device 80 is likely to be more efficient and also provides the advantage of an automated analysis. Since the field analysis is non-destructive, sample card 5 can be analyzed with another confirmatory technique after the field analysis is complete.

Preferably, sample card 5 is placed in a protective bag, such as a plastic sealable bag, labeled with any relevant identifying information and sent to a laboratory for further analysis.

The sample from sample card 5 can be analyzed by a technique that simply identifies the presence of metals, e.g., inductively coupled plasma or atomic absorption spectroscopy. This can involve cutting out sample substrate 35 and the sampling adhesive (i.e., adhesive portion 305) for specific analysis. It can also further involve some sample preparation that digests the entire sample including sample substrate 35 and adhesive portion 305, e.g., with hydrofluoric acid and microwave digestion. Other analytical techniques, either destructive or non-destructive, may be used to garner any chemical or physical information of interest.

The sample can also be analyzed with SEM, which is the currently accepted method of identifying residue as specific to GSR, as opposed to being from other environmental sources of the heavy metals. Adhesive component 300 (i.e., adhesive portion 305) can be analyzed directly on the microscope after lifting it off of sample substrate 35. A sample processing step may be needed to re-wet sample substrate 35 to allow a clean liftoff of adhesive portion 305 without tearing sample substrate 35. Sample substrate 35 can also be analyzed directly. In addition, adhesive portion 305 and sample substrate 35 can be ashed (e.g., in a crucible under high temperature, which volatizes all organic components leaving only the inorganic residue). The remaining material is then analyzed, usually by collecting the material on a separate adhesive, which is then analyzed in the microscope.

Alternatively, a field presumptive test can be used that targets nitrates. While the main disadvantage of targeting nitrates was discussed above (i.e., false positives), there are advantages that make for a useful presumptive field test in combination with a confirmatory test. Nitrates may be present in the primer (e.g., from barium nitrate, or even explosives such as RDX, PETN, DNT), but are almost always present in the propellant (from nitrocellulose, etc.) and, therefore, are usually more prevalent and leave a larger amount of residue on a shooter's hand and surrounding surfaces. As a result, in a colorimetric test that is visually interpreted, detection of nitrates can be easier to visualize.

There are several known colorimetric tests for nitrates. One common test is based on a diphenylamine test in a strong acid, often 70% sulfuric acid, in which the diphenylamine likely dimerizes or oligomerizes to produce a colored polyaniline. The strength of the acid necessary for this test will "consume" the sample, or degrade the metal particles, such that a SEM analysis can no longer yield information useful to law enforcement, namely, particle composition and morphology. SEM is the current analytical method used by law enforcement because it can identify "GSR characteristic" particles, i.e., ones that contain each of lead, barium, and antimony (primer components). This identifies the metal particles as originating from a fired bullet and distinguishes them from environmental sources of lead and other particles. However, strong acids can dissolve these particles and thereby eliminate any particles composed of multiple metals. Therefore, a colorimetric nitrate test that does not require a strong acid is necessary for a presumptive identification of GSR that could subsequently be used in a confirmatory test.

In one embodiment, aryl amines are used in a field presumptive GSR test, and then further confirmatory testing is performed using this type of chemistry. Aryl amines can be oxidized to cause a color change through the loss of an electron, most likely a non-bonded electron on a nitrogen, to produce a. colored radical cation that is resonance-stabilized. Wurster's blue and Wurster's red are two such redox compounds that detect strong oxidizing compounds, including nitrates and GSR, by turning color in their presence. For the field test, a solution of these, or similar aryl amines, can be prepared in organic solvents, or aqueous-organic solvent, and even mildly acidic solutions. This solution can be located in test capsule 25, for example. Alternatively, the aryl amine can be located in absorbent pad 45 or sampling substrate 35. Oxygen scavengers can also be incorporated into the solution to prevent or slow oxidation due to any dissolved oxygen or other oxidizers. The color change usually occurs within seconds to minutes if a collected sample contains GSR or another sufficiently strong oxidizer. Ideally, sampling substrate 35 is kept moist throughout the detection time to prevent air oxidation of the aryl amine. If adhesive component 300 is used in sample collection, then a surfactant is preferably used, especially if water is present in the solution, to improve wetting of adhesive component 300 and mixing of the solution and sample.

In another embodiment, a combination sample card is provided that contains presumptive colorimetric tests for both the metal and nitrate components of GSR. Such a sample card contains both the rhodizonate salt and the aryl amine within the sample card. For example, if Wurster's blue is the aryl amine used, a user looks for a red color to indicate the presence of the metal residue, and also looks for blue from the nitrate residue. Alternatively, reader device 80 can be used for automated detection. The overall configuration of the sample card and components is optimized for materials compatibility and chemical stability.

While there are environmental sources of false positives for the nitrate test, as there are for the diphenyl amine test, the milder conditions used to create the colored radical cation aryl amines allow for subsequent confirmatory analysis, such as through SEM. As a result, another potential tool for law enforcement is provided. Whether separate sample cards are used for the metal and nitrate tests or these tests are performed on a single sample card, immediate and orthogonal information is obtained. Because the two chemical tests target different chemical species, a positive result on both provides increased evidence of the presence of GSR. After the presumptive field test, confirmatory results can be obtained, and, importantly, this can be done for both positive and negative field tests, since these presumptive tests do not have the same sensitivity as SEM or other analytical instrumentation.

Based on the above, it should be readily apparent that the system and method of the invention provides an efficient and effective arrangement for optically detecting one or more target analytes through capillary action. The device is simple to use wherein, in general, a person need merely collect a sample by swiping the swipe area on a surface and/or using an adhesive to dab a surface, such as someone's hand, and then puts the card into the card carrier. Thereafter, the liquid containing ampoule within the card, which contains the ink solution, is crushed when a door to the optical reader device is closed. This causes ink to pass to the absorbent pad, which distributes a flow of ink to the chromatography paper on the swipe area. The ink then wicks up through the sample paper to the viewing window carrying the sample with it. The ink will dissolve explosives/narcotics/gunshot residue or other analytes and continue to pass to the viewing area on the other side of the card, while dirt and other contaminants do not enter the viewing area, thus simplifying the viewing analysis. White light is applied to the viewing area to determine when the ink hits a particular point, triggering a fan to be activated to dry the ink. Next, light is applied to the viewing area and a camera images the viewing area, sending a signal to a computer processor which has software used to analyze the signal based on the sensing of an identifying mark provided on the card which sets the analysis protocol. The system then outputs either an indication that an analyte has been found or has not been found. Preferably, the signal sent by the camera is a fluorimetric or colorimetric signal, but also could incorporate spatial analysis looking for streaks that are often present in nitrate explosives. Overall, a user need only turn the power on, put a sample containing card in the reader device, subsequently close the door, and wait for a red or green light to indicate whether or not contraband is present.

Although described with reference to exemplary embodiments of the invention, it should be understood that various changes and/or modifications can be made to the invention without departing from the spirit thereof. For instance, the sample card may have a cap or protective cover (shown but not labeled), which is completely or partially removable, to prevent contact with the sample collection area and/or sampling area, prior to analysis. This can also serve to protect these areas post-analysis from damage or from user contact, and prevent the sample substrate from contaminating other objects. For example, it is possible to provide a protective cover which is attached to the housing and contains a flap that lies over the sample collection area to prevent contamination and user contact. The flap, or even the entire cover, can be designed to be automatically lifted upon coupling of the sample card to the reader device and automatically closed when the card is removed from the reader device. In addition, reader device 80 can be designed to update firmware. Allowing the firmware to be updated allows improved algorithms to be uploaded into the system for data analysis (signal processing, lighting conditions, drying/heating procedure, etc.). As new sample cards become available for additional target analytes, firmware upgrades will upload the corresponding algorithms for the new sample cards, thus allowing existing hardware to be used for the new capabilities. Furthermore, the reader device may also have wireless capability for image transfer, as well as remote logins for diagnostic work. USB will also allow logins for diagnostic work and could eventually become an interface to a smart interface to extract forensic information. Finally, the reader device can contain an ambient light sensor, particularly to sense if there is stray light in the device which would warrant an adjustment in lighting parameters for consistent performance.

We claim:

1. A method of detecting an analyte comprising:
    collecting a sample on a sample card by wiping the sample with the sample card, said sample card containing a sample substrate, an absorbent pad and at least one test capsule containing a liquid, wherein at least one of the sample substrate, the absorbent pad and the at least one test capsule contains detection reagents;
    coupling the sample card to a card carrier of a reader device;
    performing a detection cycle including: releasing the liquid of the at least one test capsule, whereby the liquid dissolves the detection reagents contained in the sample card and delivers said reagents to the sample, causing a chemical reaction between the sample and the detection reagents to occur; and assessing an optical signal produced by the chemical reaction of the sample and the detection reagents in establishing a test result; and
    analyzing the sample using a second device that is distinct from the reader device.

2. The method of claim 1, wherein analyzing the sample using a second device includes analyzing the sample using a scanning electron microscope.

3. The method of claim 1, wherein analyzing the sample using a second device includes analyzing the sample using one of mass spectrometry, inductively coupled plasma, and atomic absorption.

4. The method of claim 1, wherein collecting the sample on the sample card includes collecting a sample on an adhesive component, the method further comprising:
    coupling the adhesive component to the sample substrate prior to coupling the sample card to the card carrier of the reader device.

5. The method of claim 4, wherein coupling the adhesive component to the sample substrate includes:
    coupling a first adhesive portion of the adhesive component to the sample substrate; and
    coupling a second adhesive portion of the adhesive component to a rear portion of the sample card.

6. The method of claim 4, further comprising:
    collecting a second sample on the sample substrate.

7. The method of claim 1, wherein collecting the sample on the sample card includes collecting a sample containing explosives, narcotics, gunshot residue, organophosphate reagents or toxic industrial chemicals.

8. A method of detecting an analyte comprising:
    collecting a sample on a sample card by wiping the sample with the sample card, said sample card containing a sample substrate, an absorbent pad and at least one test capsule containing a liquid, wherein at least one of the sample substrate, the absorbent pad and the at least one test capsule contains detection reagents, and wherein the detection reagents include a surfactant;
    coupling the sample card to a card carrier of a reader device; and
    performing a detection cycle including: releasing the liquid of the at least one test capsule, whereby the liquid dissolves the detection reagents contained in the sample card and delivers said reagents to the sample, causing a chemical reaction between the sample and the detection reagents to occur; and assessing an optical signal produced by the chemical reaction of the sample and the detection reagents in establishing a test result.

9. The method of claim 8, wherein, when the liquid of the at least one test capsule is released, the surfactant aids in solvation of metal particles, skin oils or gun cleaning oils.

10. The method of claim 8, wherein collecting the sample on the sample card includes collecting a sample on an adhesive component, the method further comprising:
    coupling the adhesive component to the sample substrate prior to coupling the sample card to the card carrier of the reader device.

11. The method of claim 10, wherein, when the liquid of the at least one test capsule is released, the surfactant reduces a surface tension of the liquid, whereby the surfactant aids in wetting the adhesive component.

12. The method of claim 1, wherein:
    causing the chemical reaction includes causing a chemical reaction to occur between the sample and at least one of a rhodizonate salt and an aryl amine; and assessing the optical signal includes assessing an optical signal produced by the chemical reaction of the sample and the at least one of the rhodizonate salt and the aryl amine.

13. The method of claim 12, wherein:
the detection reagents include an acid; and
when the liquid of the at least one test capsule is released, the acid aids in oxidation of elemental lead.

14. A method of detecting an analyte comprising:
collecting a sample on a sample card by wiping the sample with the sample card, said sample card containing a sample substrate, an absorbent pad and at least one test capsule containing a liquid, wherein at least one of the sample substrate, the absorbent pad and the at least one test capsule contains detection reagents, wherein collecting the sample on the sample card includes collecting a sample on an adhesive component;
coupling the adhesive component to the sample substrate;
coupling the sample card to a card carrier of a reader device; and
performing a detection cycle including: releasing the liquid of the at least one test capsule, whereby the liquid dissolves the detection reagents contained in the sample card and delivers said reagents to the sample, causing a chemical reaction between the sample and the detection reagents to occur; and assessing an optical signal produced by the chemical reaction of the sample and the detection reagents in establishing a test result.

15. The method of claim 14, wherein coupling the adhesive component to the sample substrate includes:
coupling a first adhesive portion of the adhesive component to the sample substrate; and
coupling a second adhesive portion of the adhesive component to a rear portion of the sample card.

16. The method of claim 14, further comprising:
collecting a second sample on the sample substrate.

17. The method of claim 14, wherein:
causing the chemical reaction includes causing a chemical reaction to occur between the sample and at least one of a rhodizonate salt and an aryl amine; and
assessing the optical signal includes assessing an optical signal produced by the chemical reaction of the sample and the at least one of the rhodizonate salt and the aryl amine.

18. The method of claim 17, wherein:
the detection reagents include an acid; and
when the liquid of the at least one test capsule is released, the acid aids in oxidation of elemental lead.

19. A method of detecting an analyte comprising:
collecting a sample on a sample card by wiping the sample with the sample card, said sample card containing a sample substrate, an absorbent pad and at least one test capsule containing a liquid, wherein at least one of the sample substrate, the absorbent pad and the at least one test capsule contains detection reagents, wherein the detection reagents include a surfactant, and wherein collecting the sample on the sample card includes collecting a sample on an adhesive component;
coupling the adhesive component to the sample substrate;
coupling the sample card to a card carrier of a reader device;
performing a detection cycle including: releasing the liquid of the at least one test capsule, whereby the liquid dissolves the detection reagents contained in the sample card and delivers said reagents to the sample, causing a chemical reaction between the sample and the detection reagents to occur; and assessing an optical signal produced by the chemical reaction of the sample and the detection reagents in establishing a test result; and
analyzing the sample using a second device that is distinct from the reader device.

20. The method of claim 1, further comprising removing the sample from the sample card prior to analyzing the sample using the second device.

21. The method of claim 20, wherein removing the sample from the sample card includes removing the sample substrate from the sample card.

22. The method of claim 14, further comprising:
removing the sample from the sample card; and
after removing the sample from the sample card, analyzing the sample using a second device that is distinct from the reader device.

23. The method of claim 22, wherein removing the sample from the sample card includes removing the adhesive component from the sample card.

24. The method of claim 1, wherein:
the sample card includes a housing;
at least a portion of the sample substrate onto which the sample is to be collected is configured to be exposed from outside the housing; and
collecting the sample on the sample card includes swiping the sample substrate across a surface.

25. The method of claim 8, wherein:
the sample card includes a housing;
at least a portion of the sample substrate onto which the sample is to be collected is configured to be exposed from outside the housing; and
collecting the sample on the sample card includes swiping the sample substrate across a surface.

26. The method of claim 16, wherein:
the sample card includes a housing;
at least a portion of the sample substrate onto which the sample is to be collected is configured to be exposed from outside the housing; and
collecting the second sample on the sample substrate includes swiping the sample substrate across a surface.

27. The method of claim 1, wherein the reader device includes a rupture mechanism, and releasing the liquid of the at least one test capsule includes rupturing the at least one test capsule with the rupture mechanism.

28. The method of claim 8, wherein the reader device includes a rupture mechanism, and releasing the liquid of the at least one test capsule includes rupturing the at least one test capsule with the rupture mechanism.

29. The method of claim 14, wherein the reader device includes a rupture mechanism, and releasing the liquid of the at least one test capsule includes rupturing the at least one test capsule with the rupture mechanism.

* * * * *